United States Patent
Stoll

Patent Number: 5,104,320
Date of Patent: Apr. 14, 1992

[54] PRECIOUS METAL TOOTH FACINGS

[76] Inventor: Robert P. Stoll, 19 Little Bay Harbor, Ponte Vedra Beach, Fla. 32082

[21] Appl. No.: 406,270

[22] Filed: Sep. 11, 1989

[51] Int. Cl.$^5$ .......................... A61C 5/08; A61C 13/08
[52] U.S. Cl. ...................................... 433/206; 433/218
[58] Field of Search ............... 433/206, 207, 215, 218, 433/219, 223

[56] References Cited

U.S. PATENT DOCUMENTS

| | | | |
|---|---|---|---|
| 712,648 | 11/1902 | Callaway | 433/219 |
| 1,393,166 | 10/1921 | Roumeguere | 433/206 |
| 1,711,402 | 4/1929 | Berger | 433/223 |
| 1,803,680 | 5/1931 | Schwartz | 433/223 |
| 1,916,321 | 7/1933 | Jaques | 433/219 |
| 3,102,337 | 9/1963 | Mintz | 433/223 |
| 3,760,502 | 9/1973 | Hirsch | 433/218 X |
| 3,986,261 | 10/1976 | Faunce | 32/12 |
| 4,632,660 | 12/1986 | Jurim | 433/215 |
| 4,764,117 | 8/1988 | Yamashita et al. | 433/215 |

FOREIGN PATENT DOCUMENTS 60775 1/1955 France ................................ 433/206

Primary Examiner—Robert P. Swiatek
Assistant Examiner—Nicholas D. Lucchesi
Attorney, Agent, or Firm—Steven R. Scott

[57] ABSTRACT

Dental facings or veneers preformed from precision metals; suitable for attachment to the labial enamel surface of human teeth; and utilizable for cosmetic purposes and/or as a base for further decorative enhancement by cut-out design, inlaid design or otherwise.

8 Claims, 2 Drawing Sheets

PRECIOUS METAL TOOTH FACINGS

BACKGROUND OF THE INVENTION (1) Field of the Invention

This invention relates generally to dental veneers for attachment to the labial enamel surfaces of human teeth. More specifically, it is concerned with the provision and application of dental veneers composed of precious metals.

(2) Description of the Prior Art

The use of precious metal crowns for aesthetic as well as functional purposes in the restoration of stained, damaged or defective teeth is well-known in prior art. More recently, dental veneers or facings of ceramic and plastic materials have come into general usage. Unlike crowns, such veneers do not cover all or a major portion of exposed tooth area. Instead, they are generally utilized to provided a cosmetic and/or prosthetic covering for labial and incisal tooth surfaces alone. As will be explored in more detail below, this technique has numerous advantages to the patient.

The evolution of technology for the production and utilization of dental facings can easily be traced by a review of the following selected patents:

| | |
|---|---|
| D. A. Zurbigg | U.S. Pat No. 1,265,022 |
| J. L. P. Roumeguere | U.S. Pat No. 1,393,166 |
| S. J. Infante | U.S. Pat No. 2,700,822 |
| Faunce | U.S. Pat No. 3,986,261 |
| Cohen et al. | U.S. Pat No. 4,226,593 |
| McClure | U.S. Pat No. 4,552,779 |

The first patents in this area involve replaceable facings for use on or with artificial teeth, crowns, or bridgework. (See, e.g., Zurbigg, Roumeguere and Infante, supra). More recently, the Faunce patent discloses a method for restoring tooth surfaces by utilizing a laminar plastic tooth facing adapted for bonding to the enamel of a patient's tooth. This technology has been eagerly adopted within the art, and preformed plastic and ceramic facings of various sizes are now readily available on the market. Cohen sets forth a method and apparatus for applying a plurality of such veneers simultaneously to a patient's teeth. In contrast to these McClure describes a process for preparing a cast metal surface for bonding to tooth structure. This methodology is adapted and explained with reference to the placement and maintenance of bridges for the retention of artificial teeth. It has not been utilized with regard to metallic tooth facings, adapted primarily for placement on the labial surface of a patient's tooth.

Where precious metals are to be utilized, as a covering for the labial surface of the tooth, patients have been generally restricted to emplacement of a crown. This is a procedure that requires the tooth to be extensively shaped by grinding in order to present a shape suitable for reception of the crown. This not only results in the loss of the integrity of the natural tooth, but is expensive and time consuming. Further, many such crowns are placed for cosmetic purposes alone. Thus, a less invasive procedure is highly desirable to preserve the function and superiority of the natural tooth.

SUMMARY OF THE INVENTION

In its preferred embodiments the present invention teaches methods and materials by which precious metals may be utilized as dental facings or veneers. The methods described include selection and application of a preformed precious metal facing manufactured by stamping sheet metal over dies or by other means. In accordance with this invention, facings in a variety of sizes and shapes can be made available for use with each tooth to meet requirements due to natural biological variations. This invention also allows the placement of facings suitable for decorative enhancement by, for example, cut out design or gem settings. A cut out design may be produced by cutting out and removing portions of the periphery of the facing such that the facing itself takes on a desired shape or design, or by cutting a desired design or shape from the interior of the facings. In the alternative, such enhanced facings may be manufactured and available for selection prior to dental placement. Bonding techniques suitable for the materials utilized may be used. The invention thereby expands the range of manufactured facings available for dental use to include precious metals as well as plastics and ceramics. Prior to application however, the surfaces of the tooth to which the facings are to be affixed must be appropriately prepared for bonding by etching with acid or other means well-known in the art. The surface of the facing which is to proximately contact the tooth must, likewise, be roughened by chemical or physical means.

DETAILED DESCRIPTION

Figure 1:
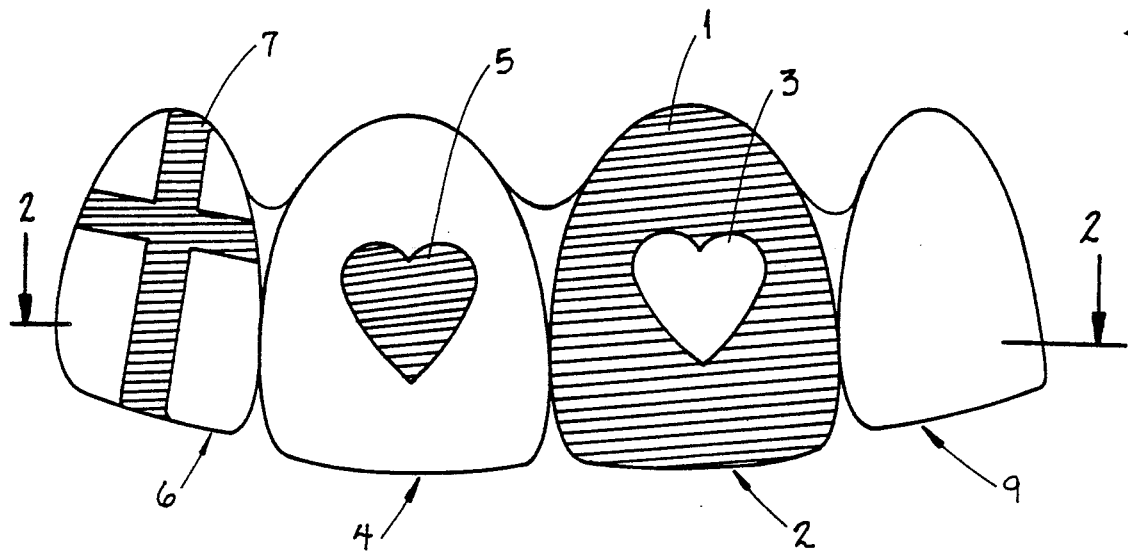
FIG. 1 provides an elevational view of a portion of an upper jaw from the facial side, with precious metal facings secured on three teeth thereof in accordance with this invention.

FIG. 1 illustrates a variety of precious metal veneers the labial surface of produced and placed, in accordance with this invention, on upper central and lateral incisor teeth. A left central incisor 2 is shown with a facing 1 covering all of its labial surface except for that exposed by a centrally located heart shaped cut-out 3. A right central incisor 4 is shown with a heart shaped facing 5 covering only a portion of its labial surface. This shape could be created by cutting out and removing the unwanted portions of a facing designed to cover the entire labial surface. Alternately, it could be produced in this form by using a die stamp, an appropriately shaped mold or by any other technique suitable to the material. A right lateral incisor 6 is shown with a cross shaped facing 7. This facing shape may be simply and easily produced by cutting out and removing the corners of a full labial facing or by any of the other methods previously mentioned. In contrast to all of the foregoing, a left lateral incisor 8 is shown without any type of facing. Facings 1, 5 and 7, illustrated in FIG. 1 would have been previously selected from a stock supply of such facings manufactured within a range of possible sizes for each human tooth. Although facing 1 covers the labial, incisal and proximal surfaces, variations of the facing could cover only the labial surface and incisal edge, labial surface and proximal edge, labial surface alone, or a portion of the labial surface. Such facings can be manufactured using techniques well-known in the metallurgical arts. Wide variations are possible in the median thicknesses of the metal used. However, as minimal treatment and reduction of enamel is contemplated by this invention, long term comfort of the patient will be maximized by the use of a facing having a thickness of one-half (½) mm or less. The patient's comfort must, nonetheless, be balanced against the qualities of the material utilized Thus, if the patient or situation favors the use of softer less durable precious metal alloys, a thicker facing and consequent reduction of enamel depth under the facing may be required to assure that the facing will have sufficient strength to withstand normal wear.

Figure 2:
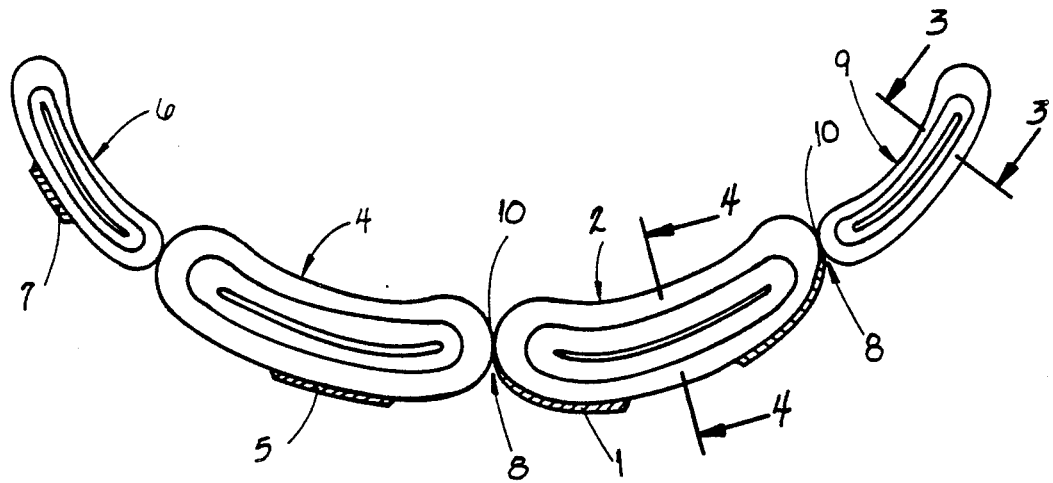
FIG. 2 is a cross-sectional view taken along the line 2—2 of FIG. 1

FIG. 2 provides a cross-sectional view of the teeth and facings illustrated in FIG. 1. It also illustrates the manner in which the facing 1 may be advantageously extended through the interproximal contact 8 between the tooth 2 to which it is applied and adjacent teeth 4 and 9. Although the facing 1 described herein may be restricted in size to cover only the labial surface of the tooth 2, the configuaration shown assures that all visible enamel is covered while placing the side margins 10 of the facing 1 in relatively self cleaning areas. By increasing the surface area bonded to the tooth 2 and wrapping around the tooth 2, this configuration also provides a stronger more durable bond between the facing 1 and the tooth 2. Space for the facing 1 may be created, if necessary, by reducing the thickness of the enamel in the contact area 8. Assuming the facing 1 utilized is of optimum size of less than one-half (½) mm, a reduction of this amount will typically be required. It will also be noted that the median thickness of the facing 1 tapers to a knife-edge at its side margins 10, allowing it to merge smoothly with the tooth surface. This is advantageous as it does not provide a "ledge" for the accumulation of food, or to serve as a point of purchase for shearing forces developed during mastication.

Figure 4:
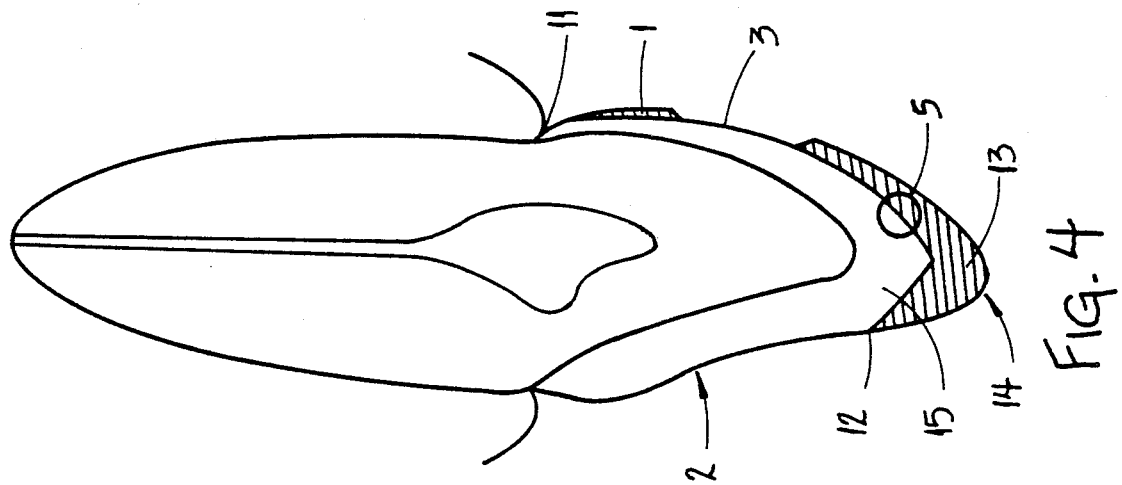
FIG. 4 is a para-saggital view taken along the line 4—4 of FIG. 2.
Figure 3:
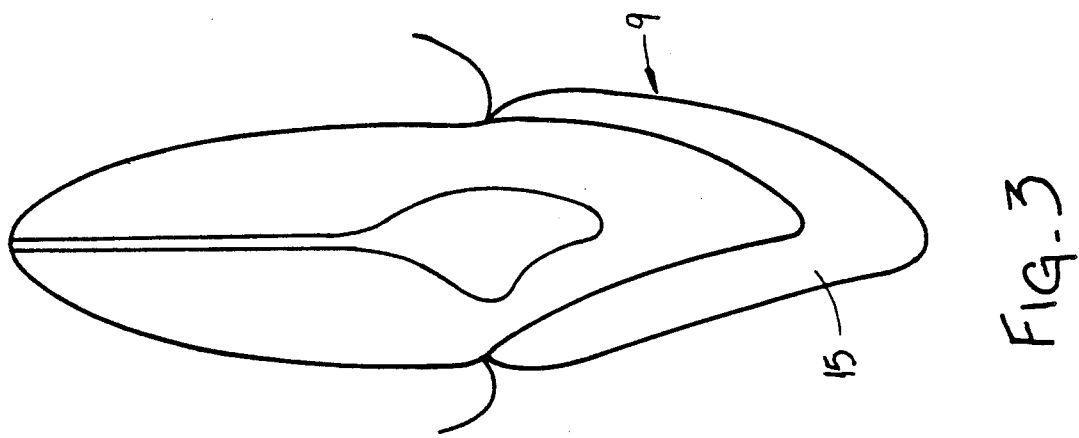
FIG. 3 is a para-saggital view taken along the line 3—3 of FIG. 2.

FIG. 3 shows the para-saggital view of unaltered tooth 9 for comparison with the para-saggital view of a tooth 2, as shown in FIG. 4, which has been prepared and fitted with facing 1 in accordance with this invention. As reflected in FIG. 4, the facing 1 is finished to a knife-edge both at the gingival margin 11 and at its lingual margin 12; however, it is produced with a thickened portion 13 at its incisal edge 14. This provides greater bulk of metal at the incisal edge 14, allowing it to resist incisal and occlusal forces during mastication. It also requires reduction of enamel and beveling of the tooth in region 15 to allow a proper fit of the facing 1 in this region.

After selection of an appropriate facing 1, it may be necessary to trim and prepare the edges of same with scissors, shears or rotating instruments to effect the desired fit to the labial and buccal surfaces of the tooth 2. This operation may be suitably performed in conjunction with a reduction of enamel in the manner previously described. After completion of these steps, the enamel surfaces of the tooth 2 that are to be covered should generally be etched prior to bonding by the use of acids commonly used for this purpose in the art. It is anticipated that facings prepared in accordance with this invention will, prior to distribution, have their inner surfaces roughened by chemical or physical means. These processes create a micrortentive surface to which a suitable bonding agent can adhere. Bonding agents suitable for use with precious metals, may then be applied in their ordinary manner to effect a bond between the teeth and facings.

Figure 5:
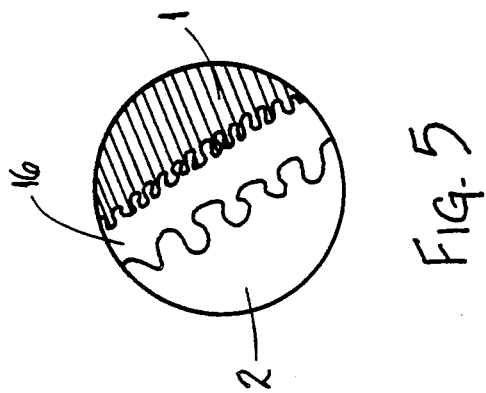
FIG. 5 is an enlarged fragmentary view of that area encompassed by circle 5 of FIG. 4.

FIG. 5 illustrates the interface between the tooth 2 and the facing 1 with bonding material 16 between the irregular, roughened surfaces of each. The precious metal facings described in this patent include facings formed from precious metal alloys where precious metals predominate. In this area as in other respects, however, wide variation is possible without exceeding the ambit of this invention.

I claim:

1. A precious metal tooth facing, comprising: a generally sheet-like body of preformed precious metal capable of being readily molded by the application of physical pressure to appropriate portions thereof so as to cover and conform to the surface contour and the shape of the tooth surfaces to which it is to be bonded having an outward surface, a roughened concave inward surface substantially conforming to the surface contour of a portion of the labial tooth surface to which it is to be bonded, and knife edges at edges between said outward and inward surfaces adapted to provide a smooth, ledgeless transition between the aforesaid facing and the enamel of the tooth to which it is bonded.

2. A precious metal tooth facing as recited in claim 1, wherein said facing substantially conforms to the shape of the entire labial surface of the tooth to which it is to be bonded.

3. A precious metal tooth facing as recited in claim 2, further comprising: proximal extentions capable of being readily molded by the application of physical pressure to appropriate portions thereof so as to cover and conform to the surface contour and the shape of the proximal surfaces of the tooth to which it is to be bonded.

4. A precious metal tooth facing as recited in claim 2, further comprising: an incisal extension capable of being readily molded by the application of physical pressure to appropriate portions thereof so as to cover and conform to the surface contour and the shape of the incisal edge of the tooth to which it is to be bonded.

5. A precious metal tooth facing as recited in claim 3, further comprising: an incisal extension capable of being readily molded by the application of physical pressure to appropriate portions thereof so as to cover and conform to the surface contour and the shape of the incisal edge of the tooth to which it is to be bonded.

6. A precious metal tooth facing as recited in claims 4 or 5, wherein the incisal extension of said facing is, in general, thicker than other portions of said facing.

7. A precious metal tooth facing as recited in claim 5, wherein the incisal extension of said facing is, in general, thicker than other portions of said facing.

8. A method of providing a precious metal facing for a tooth, said method comprising the steps of:
   providing a thin facing which has a roughened concave inward surface and an outward surface and which is capable of being molded by the application of physical pressure to appropriate portions thereof so as to conform more closely to the configuration of the surfaces of the tooth which are to be covered;
   altering the outlines of the thin precious metal facing by removing portions thereof as necessary to create the shape desired;

creating a knife edge where such does not already exist at edges between the outward and inward surfaces of the precious metal facing;

preparing the surfaces of the tooth to be covered by application of an appropriate dental agent used for the purpose of etching and roughening the enamel of the tooth;

disposing an appropriate quantity of a suitable dental bonding agent between the thin precious metal facing and the surfaces of the tooth to which it is to be bonded;

physically pressing and applying said thin precious metal facing to the surfaces of the tooth to which it is to be bonded;

molding the shape of the thin precious metal facing to more closely conform to the shape of the tooth surfaces to which it is to be bonded by applying physical pressure to appropriate portions thereof;

removing any excess bonding agent pressed from between the thin precious metal facing and the surfaces of the tooth to which it is bonded.

* * * * *